United States Patent [19]

Rieve et al.

[11] 4,029,715

[45] June 14, 1977

[54] PREPARATION OF ETHYL BENZENE

[75] Inventors: Robert W. Rieve, Springfield; Harold Shalit, Drexel Hill, both of Pa.

[73] Assignee: Atlantic Richfield Company, Los Angeles, Calif.

[22] Filed: Aug. 24, 1976

[21] Appl. No.: 717,318

[52] U.S. Cl. .................. 260/668 D; 260/669 R; 260/666 A

[51] Int. Cl.² ........................................ C07C 15/04

[58] Field of Search ............ 260/668 D, 669 R, 673

[56] References Cited

UNITED STATES PATENTS

| | | | |
|---|---|---|---|
| 2,289,916 | 7/1942 | Komerewsky | 260/668 D |
| 2,376,985 | 5/1945 | Voorhees | 260/669 R |
| 2,438,041 | 3/1948 | Dutcher | 260/669 R |
| 3,903,185 | 9/1975 | Vogel et al. | 260/668 D |

Primary Examiner—Veronica O'Keefe
Attorney, Agent, or Firm—John R. Ewbank

[57] ABSTRACT

A $C_8$ cyclic olefin stream resulting from the dimerization of butadiene is dehydrogenated for highly selective preparation of ethyl benzene and hydrogen by directing a reactant stream consisting of a major amount of an inert gas such as nitrogen and a minor amount of said $C_8$ cyclic olefin through a reaction zone having a cobalt molybdate on alumina catalyst containing 0.9-3% potassium oxide. The ethyl benzene is of suitable purity for manufacture of styrene therefrom.

1 Claim, No Drawings

PREPARATION OF ETHYL BENZENE

FIELD OF INVENTION

This invention relates to the preparation of ethyl benzene by the dehydrogenation of 4 vinyl cyclohexene-1 and to the dehydrogenation of $C_8$ cyclic olefins derived from dimerization of butadiene and to the overall process of converting butadiene to styrene.

PRIOR ART

Vogel et al U.S. Pat. No. 3,903,185 describes the preparation of ethyl benzene from vinyl cyclohexene and/or the cyclic olefins mixture derived from dimerization of butadiene. The references cited therein and discussed therein clarify the variety of difficulties which have plagued the engineers dealing with this general process.

The market for butadiene has limits which are not significantly responsive to lower prices. Accordingly any plant faced with capacity to produce an amount of butadiene larger than it has an attractive market for is interested in the conversion of the butadiene to a material for which a large market exists. The demand for styrene has been sufficiently great that there have been various proposals for the conversion of butadiene to styrene by a series of steps comprising the dehydrogenation of vinyl cyclohexene to ethyl benzene.

Butadiene is a relatively costly chemical. Because of the high price of butadiene, the selectively of a process for the conversion of butadiene to ethyl benzene is particularly important. Moreover the purity of the product and its suitability as a feed for a styrene production plant is among the desiderata.

Some of the earlier literature such as Russian patent 279,614 give inadequate information about the selectivity and yield when dehydrogenating vinyl cyclohexene at about atmospheric pressure in the presence of nitrogen over a catalyst containing iron, chromium and potassium at a temperature from about 350° to about 500° C. Vogel et al U.S. Pat. No. 3,903,185 recommends the use of up to about 100 moles of hydrogen per mole of hydrocarbon at an elevated pressure for the purpose of depressing deposition of coke in the catalyst. Although the Vogel et al patent places considerable emphasis on the advantages of using a supported platium catalyst, there is also disclosure of the use of a cobalt molybdate on alumina type of catalyst.

Prior art technologists persisted in efforts to improve the production of ethyl benzene from vinyl cyclohexene, but encountered a series of obstacles.

SUMMARY OF THE INVENTION

In accordance with the present invention, a stream of $C_8$ cyclic olefins derived from the dimerization of butadiene is dehydrogenated to form a stream of ethyl benzene by passage of a mixture of a major amount of an inert gas selected from nitrogen, steam, carbon dioxide, argon, and mixtures thereof, and a minor amount of $C_8$ cyclic olefins through a catalytic zone containing a bed of particles of alumina-supported cobalt molybdate having a potassium oxide content within the range from about 0.9% to about 3% at a temperature within the range from about 400° C to 450° C at a pressure from about 0.4 to about 4 atmosphere, the stream entering the reaction zone being substantially free from hydrogen.

The invention is further clarified by reference to plurality of examples.

EXAMPLE 1

A reactant stream containing the vapors of cyclic $C_8$ olefins is directed through a catalytic dehydrogenation zone having a bed of particles of alumina supported cobalt molybdate. The cyclic olefin stream had been prepared by the dimerization of butadiene. Said cyclic olefin stream contained a major amount of 4-vinyl cyclohexene-1. In Control A, the catalyst did not have potassium oxide and the reactant stream entering the catalytic zone contained hydrogen. In Control B, the catalyst contained 1% potassium oxide and hydrogen was present in the reactant stream A comparison of Control B and Control A shows that selectively for ethyl benzene in the presence of hydrogen was significantly reduced by using $K_2O$ in the catalyst for Control B. In Example 1, the catalyst contained 1% potassium oxide, and nitrogen was utilized as the carrier gas so that hydrogen was absent from the stream entering the reactor. The superior results achieved by Example 1 over Controls A and B are commercially significant. Data relating to these runs are shown in Table 1.

Table 1

|  | Control A | Control B | Ex. 1 |
|---|---|---|---|
| Cat. Wt. (g) | 37.6 | 35.1 | 35.1 |
| Vol. (cc) | 50.0 | 50.0 | 50.0 |
| $K_2O$ in Cat., % | 0.0 | 1.0 | 1.0 |
| Temp. ° F | 785 | 788 | 788 |
| Total Press. (psig) | 120 | 50 | 50 |
| LHSV | 1.4 | 1.2 | 1.2 |
| $H_2$/HC unit molar ratio | 10 | 15 | — |
| $N_2$/HC unit molar ratio | — | — | 15 |
| Hours on Stream | 2 | 2 | 6 |
| Wt. Balance | 94.5 | 96.7 | 99.2 |
| Product Dist. NLB (wt %) |  |  |  |
| $H_2$ | — | — | 1.5 |
| $C_1$-$C_3$ | 1.3 | 3.2 | 0 |
| $C_5$-$C_7$ | 5.8 | 7.7 | 2.3 |
| Ethyl Benzene | 85.4 | 61.6 | 91.0 |
| Styrene & Heavies | 4.6 | 1.2 | 2.3 |
| Conversion | 99.7 | 100 | 100 |
| Selectivity for EB | 85.6 | 61.6 | 91.0 |

The data show that the use of nitrogen instead of hydrogen as a carrier gas led to a higher selectively for ethyl benzene. Of particular importance the ethyl benzene had a purity sufficient to permit its use as a starting material for the preparation of styrene. Moreover the superior performance over a prolonged period established that the catalyst stability for the process was within the range of commercial attractiveness.

EXAMPLE 2

A technical grade of 4-vinyl cyclohexane-1 was processed for ethyl benzene production to obtain results substantially as described in connection with Example 1. substantially as described in connection with Example 1.

EXAMPLE 3

In further investigating the effect of miscellaneous $C_8$ cyclic olefins as components of the feed for the preparation of ethyl benzene, a mixture was prepared consisting of about 90.3% 4-vinyl cyclohexene-1 and about 9.7% cyclooctane. This mixture was vaporized in a stream containing a unit mole ratio of nitrogen to hydrocarbon of about 10 and directed through a catalyst bed having particles of said cobalt molybdate on alumina containing 1% potassium oxide. The dehydrogenation reaction was conducted at a temperature of about 400° C at a pressure of about 4 atmospheres at a liquid hydrocarbon space velocity of about 1.2 to provide 89.2% selectivity for ethyl benzene based upon conversion of feedstock. This advantageously high selectivity confirmed other evidence establishing that the miscellaneous hydrocarbons resulting from the dimerization of butadiene are convertible to ethyl benzene in a commercially attractive yield.

EXAMPLE 4

A reactant stream consisting of 55% by volume carbon dioxide and 45% by volume 4-vinyl cyclohexene-1 is directed downwardly through a catalyst bed consisting of particles containing 0.9% $K_2O$, 12% CoO, and 18% $MoO_3$ and 69.1% $Al_2O_3$ at a pressure of 8 atmospheres at a temperature of 440° C to produce ethyl benzene at a selectivity of about 90%.

EXAMPLE 5

A catalyst bed consisting of particles of gamma alumina impregnated with 20% $MoO_3$, 7% CoO and 3% $K_2O$ is employed at 405° C for dehydrogenating a stream of 4-vinyl cyclohexene-1 admixed with 19 volumes of steam (the 4-vinyl cyclohexene-1 amounting to 5% by volume of the mixture) at about 0.5 atmosphere pressure and at a LHSV of about 1 to produce ethyl benzene at a selectivity of about 92%.

EXAMPLE 6

A mixture of 6 volumes of argon and 1 volume of 4-vinyl cyclohexene-1 is directed through a catalyst bed containing particles of gamma alumina impregnated with 10% $C_oO$, 12% $MoO_3$ and 2% $K_2O$ at a pressure of 4 atmospheres at 420° C at LHSV of 4 to prepare ethyl benzene at a selectivity of about 90%. Substantially the same results are obtained when an inert gas prepared by removing residual oxygen and combustibles from a flue gas and containing the argon derived from air and the steam and carbon dioxide from flue gas, is employed as the inert gas.

EXAMPLE 7

Butadiene is dimerized and the dimer separated by distillation into linear dimer and cyclic $C_8$ olefins. The $C_8$ cyclic olefins are vaporized and mixed with an equamolar mixture of nitrogen, steam, carbon dioxide, and argon to provide an inert gas to hydrocarbon unit mol ratio of 3 and directed through a bed of catalyst particles containing 12% $C_oO$, 22% $MoO_3$, 1% $K_2O$, 1% $SiO_2$ stabilizer, and 64% sorptive alumina. The pressure is atmospheric and the temperature is 448° C. The selectivity for formation of ethyl benzene is 91%. The purity of the ethyl benzene is sufficiently high that it is employed as feedstock for the formation of styrene by dehydrogenation over an alumina supported platinum catalyst.

It should be noted that the examples merely illustrate appropriate embodiments of the invention, which is concerned with a method of preparing ethyl benzene which consists of directing the vapors of cyclic $C_8$ olefin hydrocarbon steam rich in 4-vinyl cyclohexene-1 together with an inert gas selected from the group consisting of nitrogen, steam, carbon dioxide, argon, and mixtures thereof, as a reactant stream toward a fixed bed of catalyst particles, said reactant stream being substantially free from hydrogen; directing said reactant stream through a fixed bed of particles consisting of alumina-supported oxides of cobalt, molydenum and potassium, the concentration of potassium oxide being within a range from about 0.9% to about 3%, said bed of particles being maintained at a pressure within a range from about 0.4 to 8 atmospheres and a temperature within a range from about 400° C to about 450° C, the liquid space rate of $C_8$ hydrocarbons with respect to said bed of particles being within a range from about 0.5 to about 3.0 volumes of liquid per volume of catalyst bed per hour; and recovering ethyl benzene from the effluent from said catalyst bed.

We claim:

1. The method of preparing ethyl benzene which consists of:

directing a stream of $C_8$ cyclic olefin hydrocarbon vapors rich in 4-vinyl cyclohexene-1, together with a larger volume of an inert gas selected from nitrogen, steam, carbon dioxide, argon, and mixtures thereof as a reactant stream toward a fixed bed of catalyst particles, said reactant stream being substantially free from hydrogen;

directing said reactant stream through a fixed bed of particles consisting of alumina-supported oxides of cobalt, molydenum and potassium, the concentration of potassium oxide being within a range from about 0.9% to about 3%, said bed of particles being maintained at pressure within a range from about 0.4 to 8 atmospheres and at a temperature within a range from about b 400° C to about 450° C, the liquid space rate of $C_8$ hydrocarbons with respect to said bed of particles being within a range from about 0.5 to about 3.0 volumes of liquid per volume of catalyst bed per hour;

and recovering ethyl benzene from the effluent from said catalyst bed.

* * * * *